United States Patent [19]

Diana

[11] 4,039,575

[45] Aug. 2, 1977

[54] ALKANIMIDOYLTHIOUREAS

[75] Inventor: Guy D. Diana, Stephentown, N.Y.

[73] Assignee: Sterling Drug Inc., New York, N.Y.

[21] Appl. No.: 669,229

[22] Filed: Mar. 22, 1976

Related U.S. Application Data

[63] Continuation-in-part of Ser. No. 418,087, Nov. 21, 1973, Pat. No. 3,984,467, which is a continuation-in-part of Ser. No. 15,875, March 2, 1970, Pat. No. 3,830,839, which is a continuation-in-part of Ser. No. 711,235, March 7, 1968, Pat. No. 3,629,455.

[51] Int. Cl.$^2$ .................... C07C 157/05; A61K 31/17
[52] U.S. Cl. ............................. 260/552 R; 260/501.14
[58] Field of Search .................................... 260/552 R

[56] References Cited

U.S. PATENT DOCUMENTS

| | | | |
|---|---|---|---|
| 3,146,262 | 8/1964 | Schäfer et al. | 260/553 A |
| 3,547,937 | 12/1970 | Diana | 260/553 A X |
| 3,629,455 | 12/1971 | Diana | 260/553 A X |
| 3,790,631 | 2/1974 | Diana | 260/553 A |
| 3,830,839 | 8/1974 | Diana | 260/552 R X |
| 3,898,277 | 8/1975 | Duerr et al. | 260/552 R |

FOREIGN PATENT DOCUMENTS

| | | | |
|---|---|---|---|
| 2,003,438 | 11/1969 | France | |
| 1,175,223 | 8/1964 | Germany | 260/553 A |
| 1,938,796 | 3/1970 | Germany | 260/552 R |
| 7,021,300 | 5/1966 | Japan | 260/553 A |

OTHER PUBLICATIONS

Pinner, Chem. Ber. 28, 476 (1895).
Kurzer, J. Chem. Soc. 2854 (1959).

*Primary Examiner*—Daniel E. Wyman
*Assistant Examiner*—Thomas A. Waltz
*Attorney, Agent, or Firm*—Frederik W. Stonner; B. Woodrow Wyatt

[57] ABSTRACT

The compounds of this invention are novel alkanimidoylthioureas having antifertility activity. They are prepared by the reaction of appropriate alkanamidines with appropriate isothiocyanates.

10 Claims, No Drawings ically illustrate the invention with-

ALKANIMIDOYLTHIOUREAS

CROSS-REFERENCES TO RELATED APPLICATIONS

This application is a continuation-in-part of copending application Ser. No. 418,087, filed Nov. 21, 1973, now U.S. Pat. No. 3,984,467, in turn a continuation-in-part of application Ser. No. 15,875, filed Mar. 2, 1970, now U.S. Pat. No. 3,830,839, in turn a continuation-in-part of application Ser. No. 711,235, filed Mar. 7, 1968, now U.S. Pat. No. 3,629,455.

BACKGROUND OF THE INVENTION

1. Field of the Invention

The invention relates to novel 1-phenyl-3-alkanimidoyl-thioureas.

2. Description of the Prior Art

Pinner, Chem. Ber. 28, 476 (1895), describes the preparation of 3-phenyl-1-(heptanimidoyl)-2-thiourea. Kurzer, J. Chem. Soc. 2854 (1959), describes the preparation of 3-phenyl-1-(acetimidoyl)-2-thiourea and 3-tolyl-1-(acetimidoyl)-2-thiourea. No biological activity is disclosed for these compounds.

SUMMARY OF THE INVENTION

In one composition of matter aspect of the invention there is provided a compound selected from the group consisting of 1-(4-chlorophenyl)-3-(4,4-dimethylpentanimidoyl)-2-thiourea, 1-(4-chlorophenyl)-3-(hexanimidoyl)-2-thiourea, 1-(4-chlorophenyl)-3-(heptanimidoyl)-2-thiourea, 1-(4-bromophenyl)-3-(heptanimidoyl)-2-thiourea, 1-(4-flourophenyl)-3-(heptanimidoyl)-2-thiourea, 1-(4-iodophenyl)-3-(heptanimidoyl)-2-thiourea, 1-(3-chlorophenyl)-3-(heptanimidoyl)-2-thiourea, 1-(2,4-dibromophenyl)-3-(heptanimidoyl)-2-thiourea, 1-(2-chloro-4-methylphenyl)-3-(heptanimidoyl)-2-thiourea, 1-(4-chlorophenyl)-3-(octanimidoyl)-2-thiourea and 1-(4-chlorophenyl)-3-(nonanimidoyl)-2-thiourea, and acid-addition salts thereof.

In another composition of matter aspect of the invention there is provided a compound selected from the group consisting of 1-(4-methoxyphenyl)-3-(heptanimidoyl)-2-thiourea and 1-[4-(trifluoromethoxy)-phenyl]-3-(heptanimidoyl)-2-thiourea, and acid-addition salts thereof.

The compounds of the invention were found to possess antifertility activity when tested in rats according to the standard endocrinological evaluation procedure described hereinbelow.

DETAILED DESCRIPTION OF THE INVENTION

The compounds of the invention are prepared by reacting appropriate alkanamidines with appropriate phenyl isothiocyanates using standard procedures as described in the specific examples hereinbelow.

The following examples illustrate the invention without, however, limiting it thereto.

EXAMPLE 1

1-(4-Chlorophenyl)-3-(heptanimidoyl)-2-thiourea

A stirred mixture, prepared by reacting 3.45 g. sodium with 300 ml. dry acetone at room temperature was cooled to 5° C. and 24.7 g. heptanamidine hydrochloride was added in one portion. After twenty minutes there was added dropwise during thirty minutes, a solution of 25.4 g. 4-chlorophenyl isothiocyanate (m.p. 44°-45° C.; prepared from 4-chloroaniline) in 150 ml. dry acetone while the temperature was maintained at 0° to 5° C. The mixture was stirred for four hours at room temperature, filtered and the filtrate was evaporated to dryness under reduced pressure. A solution of the residue in 700 ml. ether was chilled and treated with ethereal hydrogen chloride until acidic and the resulting solid was filtered to give 43.1 g. 1-(4-chlorophenyl)-3-(heptanimidoyl)-2-thiourea hydrochloride; m.p. 148°-150° C. The hydrochloride salt was stirred in dilute aqueous sodium hydroxide and the resulting base was extracted with ether. The ether extract was dried and evaporated. The residue was taken up in 100 ml. n-hexane and the resulting solids were filtered and recrystallized from benzene-(n-hexane) to give 9.1 g. 1-(4-chlorophenyl)-3-(heptanimidoyl)-2-thiourea; m.p. 112°-113° C.

EXAMPLE 2

1-(4-Bromophenyl)-3-(heptanimidoyl)-2-thiourea

Following a procedure similar to that described in Example 1 and using 3.4 g. sodium in 300 ml. dry acetone, 24.7 g. heptanamidine hydrochloride, and 32.1 g. 4-bromophenyl isothiocyanate in 100 ml. acetone there was obtained 48.7 g. 1-(4-bromophenyl)-3-(heptanimidoyl)-2-thiourea hydrochloride; m.p. 171°-174° C.

An aqueous suspension of the above hydrochloride salt was treated with an excess of 1N-sodium hydroxide solution and then extracted with ether. The ether extracts were dried and evaporated to dryness under reduced pressure to yield 1-(4bromophenyl)-3-(heptanimidoyl)-2-thiourea; m.p. 112°-113° C. (from benzene-n-pentane).

The 4-bromophenyl isothiocyanate was prepared by the following procedure.

To a stirred cooled mixture of 28 g. calcium carbonate in 150 ml. each of water and ethylenedichloride was added dropwise simultaneously but separately, a solution of 50 g. 4-bromoaniline in 150 ml. ethylenedichloride and 34.5 g. thiophosgene in 150 ml. ethylenedichloride at a rate which maintained thiophosgene in slight excess over 4-bromoaniline in the reaction mixture while the temperature was maintained at 12°-15° C. When the addition was completed stirring was continued at room temperature for four hours. The organic layer was separated, washed with 5% hydrochloric acid and water, dried and evaporated to dryness. The residue was distilled under reduced pressure to give 55 g. 4-bromphenyl isothiocyanate, b.p. 142°-144° C./14 mm., m.p. 61°-62° C.

The phenyl isothiocyanates used as starting materials for the preparation of the thioureas of this invention were prepared from the corresponding known anilines following a procedure similar to that described above for the preparation of 4-bromophenyl isothiocyanate.

EXAMPLE 3

1-(4-Methoxyphenyl)-3-(heptanimidoyl)-2-thiourea

Following a procedure similar to that described in Example 2 but substituting for 4-bromophenyl isothiocyanate an equivalent amount of 4-methoxyphenyl isothiocyanate (b.p. 140°-145° C./14-17 mm; prepared from 4-methoxyaniline) there was obtained 1-(4-methoxyphenyl)-3-(heptanimidoyl)-2-thiourea, m.p.

70°–72° C. (from benzene-n-pentane); hydrochloride (27 g.), m.p. 163°–166° C.

EXAMPLE 4

1-(4-Chlorophenyl)-3-(octanimidoyl)-2-thiourea

Following a procedure similar to that described in Example 1 but using 2 g. sodium in 250 ml. dry acetone, 15.7 g. octanamidine hydrochloride, and 15 g. 4-chlorophenyl isothiocyanate in 70 ml. dry acetone there was obtained 1-(4-chlorophenyl)-3-(octanimidoyl)-2-thiourea, m.p. 98°–99° C. (from benzene-n-pentane); hydrochloride (18.7 g. ), m.p. 155°–157° C. (from acetonitrile).

EXAMPLE 5

1-(4-Chlorophenyl)-3-(hexanimidoyl)-2-thiourea

Following a procedure similar to that described in Example 1 but using 3.4 g. sodium in 300 ml. dry acetone, 22.5 g. hexanamidine hydrochloride, and 25.9 g. 4-chlorophenyl isothiocyanate in 150 ml. dry acetone there was obtained 1-(4-chlorophenyl)-3-(hexanimidoyl)-2-thiourea, m.p. 100°–102° C. (from benzene-n-pentane); hydrochloride (21 g.), m.p. 175° C. (from acetonitrile).

EXAMPLE 6

1-(4-Fluorophenyl)-3-(heptanimidoyl)-2-thiourea

Following a procedure similar to that described in Example 1 but using 1.6 g. sodium in 200 ml. dry acetone, 12.3 g. heptanamidine hydrochloride, and 11.6 g. 4-flourophenyl isothiocyanate (b.p. 48° C./0.025 mm.; prepared from 4-fluoroaniline) in 50 ml. dry acetone there was obtained 1-(4-fluorophenyl)-3-(heptanimidoyl)-2-thiourea, m.p. 75°–76° C. (from benzene-n-pentane); hydrochloride (17.1 g.), m.p. 155° C. (from acetonitrile).

EXAMPLE 7

1-(2,4-Dibromophenyl)-3-(heptanimidoyl)-2-thiourea

Following a procedure similar to that described in Example 1 but using 2.3 g. sodium in 300 ml. dry acetone, 16.5 g. heptanamidine hydrochloride, and 29.3 g. 2,4-dibromophenyl isothiocyanate (m.p. 68°–70° C.; prepared from 2,4-dibromoaniline) in 100 ml. dry acetone there was obtained 1-(2,4-dibromophenyl)-3-(heptanimidoyl)-2-thiourea, m.p. 86°–88° C. (from benzene-n-hexane); hydrochloride (14 g.), m.p. 164°–165° C. (from acetonitrile).

EXAMPLE 8

1-(4-Iodophenyl)-3-(heptanimidoyl)-2-thiourea

Following a procedure similar to that described in Example 1 but using 2.3 g. sodium in 300 ml. dry acetone, 16.4 g. heptanamidine hydrochloride, and 26.1 g. 4-iodophenyl isothiocyanate (m.p. 75°–78° C.; prepared from 4-iodoaniline) in 150 ml. dry acetone there was obtained 1-(iodophenyl)-3-(heptanimidoyl)-2-thiourea, m.p. 116°–117° C. (from benzene-n-hexane); hydrochloride (28.5 g.), m.p. 185°–187° C. (from isopropyl alcohol).

EXAMPLE 9

1-(3-Chlorophenyl)-3-(heptanimidoyl)-2-thiourea

Following a procedure similar to that described in Example 1 and using 3.4 g. sodium in 450 ml. dry acetone, 24.7 g. heptanamidine hydrochloride, and 25 g. 3-chlorophenyl isothiocyanate (b.p. 64°–65° C./0.4 mm.; prepared from 3-chloroaniline) there was obtained 1-(3-chlorophenyl)-3-heptanimidoyl)-2-thiourea, m.p. 89°–90° C. (from benzene-n-hexane); hydrochloride (34 g.), m.p. 155°–156° C. (from acetonitrile).

EXAMPLE 10

1-(2-Chloro-4-methylphenyl)-3-(heptanimidoyl)-2-thiourea

Following a procedure similar to that described in Example 1 and using 2.3 g. sodium in 250 ml. dry acetone, 16.4 g. heptanamidine hydrochloride, and 16 g. 2-chloro-4-methylphenyl isothiocyanate (b.p. 80°–82° C./0.3 mm.; prepared from 2-chloro-4-methylaniline) in 100 ml. dry acetone there was obtained 1-(2-chloro-4-methylphenyl)-3-(heptanimidoyl)-2-thiourea, m.p. 78°–80° C. (from benzene-n-pentane); hydrochloride (23 g.), m.p. 138°–140° C. (from isopropyl alcohol).

EXAMPLE 11

1-[4-(Trifluoromethoxy)phenyl]-3-(heptanimidoyl)-2-thiourea

Following a procedure similar to that described in Example 1 but using 2.3 g. sodium in 300 ml. dry acetone, 16.4 g. heptanamidine hydrochloride, and 21.9 g. 4-(trifluoromethoxy)-phenyl isothiocyanate [b.p. 88° C./7 mm.; prepared from 4-(trifluoromethoxy)aniline] in 120 ml. dry acetone there was obtained 1-[4-(trifluoromethoxy)phenyl]-3-(heptanimidoyl)-2-thiourea, m.p. 90°–91° C. (from benzene-n-pentane); hydrochloride (25.3 g.), m.p. 171°–172° C. (from acetonitrile).

EXAMPLE 12

1-(4-Chlorophenyl)-3-(4,4-dimethylpentanimidoyl)-2-thiourea

Following a procedure similar to that described in Example 1 but using 7.22 g. sodium in 705 ml. dry acetone, 51.7 g. 4,4-dimethylvaleramidine hydrochloride, and 53.2 g. 4-chlorophenyl isothiocyanate in 350 ml. dry acetone there was obtained 1-(4-chlorophenyl)-3-(4,4-dimethylpentanimidoyl)-2-thiourea; m.p. 135°–137° C. (from acetonitrile); hydrochloride (80.7 g.), m.p. 182°–186° C.

4,4-Dimethylvaleramidine hydrochloride was prepared as follows: 28.0 g. 4,4-dimethylvaleronitrile in 8.1 g. of dry methyl alcohol was treated with 52.5 ml. of ethereal hydrogen chloride (0.252 m. HCl) during ten minutes at 0° C. The mixture was kept cold overnight and the resulting solid imino-ether was filtered and slurried in absolute ethyl alcohol and 43 ml. of alcoholic ammonia (0.263 m. $NH_3$) was added over ten minutes. Cooling was applied to maintain the temperature at 25°–30° C. The mixture was stirred two hours and filtered to give 14.6 g. 4,4-dimethylvaleramidine hydrochloride; m.p. 268°–270° C.

4,4-Dimethylvaleronitrile was prepared as follows: a mixture of 30.2 g. 3,3-dimethylbutylchloride and 15 g. sodium cyanide in 75 ml. polyethylene glycol was heated at 120°–130° C. for seventy minutes. The mixture was filtered and the filtrate was distilled under reduced pressure to yield 17.4 g. 4,4-dimethylvaleronitrile; b.p. 56°–58° C./14 mm.

EXAMPLE 13

1-(4-Chlorophenyl)-3-(nonanimidoyl)-2-thiourea

Following a procedure similar to that described in Example 1 but using 1.9 g. sodium in 200 ml. dry acetone, 16 g. nonanamidine hydrochloride, and 14.2 g. 4-chlorophenyl isothiocyanate in 100 ml. dry acetone there was obtained 1-(4-chlorophenyl)-3-(nonanimidoyl)-2-thiourea, m.p. 102°–103° C. (from benzene-n-hexane); hydrochloride (16.2 g.); m.p. 172°–174° C. (from acetonitrile).

The nonanamidine hydrochloride (m.p. 113° C.) was prepared following the general procedure described in Example 12 but substituting for 4,4-dimethylvaleronitrile an equivalent amount of nonanenitrile.

In Examples 1 to 13 above, all starting materials for which a specific preparative procedure is not described are known compounds.

The molecular structure of the compounds of this invention were assigned on the basis of the method of their synthesis and study of their infrared spectra, and confirmed by the correspondence between calculated and found values for the elementary analysis for representative examples.

The carbimidoylthioureas of the invention exist in tautomeric forms which can be illustrated by the partial formulas

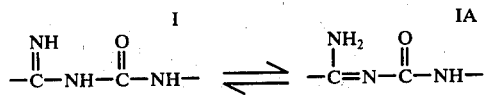

As with all tautomeric systems, the rate of transformation I $\rightleftharpoons$ IA and the ratio I/IA are dependent on the thermodynamic environment, including the state of aggregation, so that measurements by any particular technique do not necessarily have validity except under the conditions of the measurement, thereby, among other consequences, givng rise to problems for any simple designation of the physical embodiments. Thus, measurement of the infrared spectra in potassium bromide admixture and measurement of the nuclear magnet spectra are not helpful in determining which tautomeric form, I or IA is present or predominates and therefore the names based on structure I are preferred although it is understood that either or both structures I and IA are comprehended.

The novel carbimidoylthioureas of the invention can exist in either base or acid-addition salt form. The compounds in free base form, are converted to the acid-addition salt form by interaction of the base with an acid. In like manner, the free bases can be regenerated from the acid-addition salt form in the conventional manner, that is, by treating the salts with strong aqueous bases, for example alkali metal hydroxides, alkali metal carbonates, and alkali metal bicarbonates. The bases thus regenerated can then be interacted with the same or a different acid to give back the same or a different acid-addition salt. Thus the novel bases and all of their acid-addition salts are readily inter-convertible, and are the full equivalents of each other.

The free bases of the compounds of the invention and their acid-addition salts have inherent pharmacodynamic activity of a type more fully described herein. This inherent pharmacodynamic activity can be enjoyed in useful form for pharmaceutical purposes by employing the free bases themselves or the acid-addition salts formed from pharmaceutically-acceptable acids, that is, acids whose anions are innocuous to the animal organism in effective doses of the salts so that beneficial properties inherent in the common structural entity represented by the free bases are not vitiated by side-effects ascribable to the anions.

In utilizing this pharmacodynamic activity of the salts of the compounds of the invention, I prefer of course to use pharmaceutically-acceptable salts. Although water-insolubility, high toxicity, or lack of crystalline character may make some particular salt species unsuitable or less desirable for use as such in a given pharmaceutical application, the water-insoluble or toxic salts can be converted to the corresponding pharmaceutically-acceptable bases by decomposition of the salt with aqueous base as explained above, or alternatively, they can be converted to any desired pharmaceutically-acceptable acid-addition salt by double decomposition reactions involving the anion, for example, by ion-exchange procedures.

Moreover, apart from their usefulness in pharmaceutical application, the salts are useful as characterizing or identifying derivatives of the free bases or in isolation or purification procedures. Like all of the acid-addition salts, such characterizing or purification salt derivatives can, if desired, be used to regenerate the pharmaceutically-acceptable free bases by reaction of the salts with aqueous base, or alternatively can be converted to a pharmaceutically-acceptable acid-addition salt by, for example, ion-exchange procedures.

It will be appreciated from the foregoing that all of the acid-addition salts of the new bases are useful and valuable compounds, regardless of considerations of solubility, toxicity, physical form, and the like, and are accordingly within the purview of the instant invention.

The novel feature of the compounds of the invention, then, resides in the concept of the bases and cationic forms of the new imidoylthioureas and not in any particular acid moiety or acid anion associated with the salt forms of our compounds; rather, the acid moieties or anions which can be associated in the salt forms are in themselves neither novel nor critical and therefore can be any acid anion or acid-like substance capable of salt formation with bases. In fact, in aqueous solutions, the base form or water-soluble acid-addition salt form of the compounds of the invention both possess a common protonated cation or ammonium ion.

Thus the acid-addition salts discussed above and claimed herein are prepared from any organic acid, inorganic acid (including organic acids having an inorganic group therein), or organo-metallic acid as exemplified by organic mono and polycarboxylic acids, such as found, for example, in Beilstein's Organische Chemie, 4th ed., Volumes III, IV, IX, X, XIV, XVII, XIX, XXI, XXII, and XXV; organic mono- and polysulfonic and -sulfinic acids, such as found, for example, in Beilstein Volumes VI, XI, XVI, and XXII; organic phosphonic and phosphinic acids, such as found, for example, in Beilstein Volumes XI and XVI; organic acids of arsenic and antimony, such as found, for example, in Beilstein Volume XVI; organic heterocyclic carboxylic, sulfonic, and sulfinic acids, such as found, for example, in Beilstein Volumes XVIII, XXII, and XXV; acidic ion-exchange resins; and inorganic acids of any acid forming element or combination of elements, such as found in Mellor, Comprehensive Treatise on Inorganic and Theoretical Chemistry, Longman's, Green and Co., New York, N.Y. Volumes I-XVI. In addition, acetic acid, quinic acid, sulfamic acid, methanesulfonic acid, ethanesulfonic acid, isethionic acid, benzenesulfonic acid, p-toluenesulfonic acid, benzenesulfinic acid, butylarsonic acid, diethylphosphinic acid, p-aminophenylarsinic acid, phenylstibnic acid, phenylphosphinous acid, methane-phosphonic acid, phenylphosphinic acid, acidic resins, hydrofluoric acid, hydrochloric acid, hydrobromic acid, hydriodic acid, perchloric acid, nitric acid, sulfuric acid, phosphoric acid, hydrocyanic acid, phosphotungstic acid, molybdic acid, phosphomolybdic acid, pyrophosphoric acid, arsenic acid, picric acid, picrolonic acid, barbituric acid, boron trifluoride, and the like.

The acid-addition salts are prepared either by dissolving the free base in an aqueous solution containing the appropriate acid and isolating the salt by evaporating the solution, or by reacting the free base and acid in an organic solvent, in which case the salt separates directly or can be obtained by concentration of the solution.

The compounds of the invention were tested in rats by a standard endocrinological evaluation procedure described hereinbelow and were found to possess antifertility activity. They are therefore useful as antifertility agents.

TEST PROCEDURE FOR THE DETERMINATION OF ANTIFERTILITY ACTIVITY

Mature female rats were medicated daily with the test agent for two days prior to insemination by proven male rats and daily for twelve days after insemination (a total of fourteen medications). The rats were autopsied fifteen days after insemination and their uteri were removed and examined for evidence of pregnancy. The test agents were administered either as solutions or suspensions, depending on solubility and dosage level, in ten percent ethyl alcohol-cottonseed oil.

The carbimidoylthioureas of the invention were found to be effective as antifertility agents when administered subcutaneously and/or orally to female rats at 50 mg/kg × 14 days (calculated on the basis of the free base) according to the procedure described above.

The actual determination of the numeral biological data definitive for a particular compound is readily determined by standard test procedures by technicians versed in pharmacological test procedures, without the need for any extensive experimentation.

The compounds of the invention can be prepared for use by dissolving under sterile conditions a salt form of the compounds in water (or an equivalent amount of a non-toxic acid if the free base is used), or in a physiologically compatible aqueous medium such as saline, and stored in ampoules for intramuscular injection. Alternatively, they can be incorporated in unit dosage form as tablets or capsules for oral administration either alone or in combination with suitable adjuvants such as calcium carbonate, starch, lactose, talc, magnesium stearate, gum acacia, and the like. Still further the compounds can be formulated for oral administration in aqueous alcohol, glycol, or oil solutions or oil-water emulsions in the same manner as conventional medicinal substances are prepared.

I claim:

1. A compound selected from the group consisting of 1-(4-chlorophenyl)-3-(4,4-dimethylpentanimidoyl)-2-thiourea, 1-(4-chlorophenyl)-3-(hexanimidoyl)-2-thiourea, 1-(4-chlorophenyl)-3-(heptanimidoyl)-2-thiourea, 1-(4-bromophenyl)-3-(heptanimidoyl)-2-thiourea, 1-(4-fluorophenyl)-3-(heptanimidoyl)-2-thiourea, 1-(4-iodophenyl)-3-(heptanimidoyl)-2-thiourea, 1-(3-chlorophenyl)-3-(heptanimidoyl)-2-thiourea, 1-(2,4-dibromophenyl)-3-(heptanimidoyl)-2-thiourea, 1-(2-chloro-4-methylphenyl)-3-(heptanimidoyl)-2-thiourea, 1-(4-chlorophenyl)-3-(octanimidoyl)-2-thiourea and 1-(4-chlorophenyl)-3-(nonanimidoyl)-2-thiourea, and acid-addition salts thereof.

2. 1-(4-Chlorophenyl)-3-(4,4-dimethylpentanimidoyl)-2-thiourea according to claim 1.

3. 1-(4-Chlorophenyl)-3-(heptanimidoyl)-2-thiourea according to claim 1.

4. 1-(4-Bromophenyl)-3-(heptanimidoyl)-2-thiourea according to claim 1.

5. 1-(4-Fluorophenyl)-3-(heptanimidoyl)-2-thiourea according to claim 1.

6. 1-(4-Iodophenyl)-3-(heptanimidoyl)-2-thiourea according to claim 1.

7. 1-(4-Chlorophenyl)-3-(nonanimidoyl)-2-thiourea according to claim 1.

8. A compound selected from the group consisting of 1-(4-methoxyphenyl)-3-(heptanimidoyl)-2-thiourea and 1-[4-(trifluoromethoxy)phenyl]-3-(heptanimidoyl)-2-thiourea, and acid-addition salts thereof.

9. 1-(4-Methoxyphenyl)-3-(heptanimidoyl)-2-thiourea according to claim 8.

10. 1-[4-(Trifluoromethoxy)phenyl]-3-(heptanimidoyl)-2-thiourea according to claim 8.

* * * * *